United States Patent
Shin

(10) Patent No.: US 9,402,756 B2
(45) Date of Patent: Aug. 2, 2016

(54) MONORAIL

(75) Inventor: Kyong Min Shin, Seoul (KR)

(73) Assignees: TAEWOONG MEDICAL CO., LTD, Gyeonggi-do (KR); Kyong Min Shin, Seoul (KR)

(*) Notice: Subject to any disclaimer, the term of this patent is extended or adjusted under 35 U.S.C. 154(b) by 271 days.

(21) Appl. No.: 14/234,580

(22) PCT Filed: Aug. 3, 2012

(86) PCT No.: PCT/KR2012/006193
§ 371 (c)(1),
(2), (4) Date: Jan. 23, 2014

(87) PCT Pub. No.: WO2013/027940
PCT Pub. Date: Feb. 28, 2013

(65) Prior Publication Data
US 2014/0180389 A1     Jun. 26, 2014

(30) Foreign Application Priority Data

Aug. 24, 2011 (KR) .......................... 10-2011-0084435

(51) Int. Cl.
*A61F 2/06* (2013.01)
*A61F 2/95* (2013.01)
*A61F 2/966* (2013.01)
*A61M 25/01* (2006.01)

(52) U.S. Cl.
CPC . *A61F 2/95* (2013.01); *A61F 2/966* (2013.01); *A61M 2025/0183* (2013.01)

(58) Field of Classification Search
CPC .............. A61F 2/06; A61F 2/95; A61F 2/84; A61F 2/966; A61M 25/01; A61M 2025/0183; A61B 17/22
See application file for complete search history.

(56) References Cited

U.S. PATENT DOCUMENTS

| 5,389,087 A | 2/1995 | Miraki | |
|---|---|---|---|
| 2005/0080472 A1* | 4/2005 | Atkinson | A61F 2/86 607/126 |
| 2007/0112407 A1 | 5/2007 | Mertens et al. | |
| 2009/0240206 A1 | 9/2009 | Lunn et al. | |

FOREIGN PATENT DOCUMENTS

KR    1020100086294    7/2010

* cited by examiner

*Primary Examiner* — Victor Nguyen
(74) *Attorney, Agent, or Firm* — IP & T Group LLP

(57) ABSTRACT

A monorail guides a guide wire introduced into an outer tube in a catheter for stent surgery. The catheter includes the outer tube having an outer hole, an inner tube installed in the outer tube, and a guide wire inserted into the outer hole and the inner tube and protruding outwards from a front end of the inner tube so that the outer tube and the inner tube move along the guide wire so as to be guide a stent. The monorail includes a separation guide which is inserted into and fixed in the outer tube and configured such that the guide wire that is inserted into the outer hole is spaced apart from the inner tube without making contact with the inner tube.

3 Claims, 5 Drawing Sheets

MONORAIL

This application is a national stage application of PCT/KR2012/006193 filed on Aug. 3, 2012, which claims priority of Korean patent application number 10-2011-0084435 filed on Aug. 24, 2011. The disclosure of each of the foregoing applications is incorporated herein by reference in its entirety.

TECHNICAL FIELD

The present invention relates, in general, to monorails and, more particularly, to a monorail which can reliably guide a guide wire introduced into an outer tube such that an entry direction and an exit direction of the guide wire are prevented from changing.

BACKGROUND ART

Generally, catheters are a kind of medical devices which hold a stent and transfer it to a target location, that is, a lesion, to be treated.

Such a catheter is used to transfer a stent to a lesion. In detail, after the stent is installed on the catheter, it is transferred to the lesion by the catheter. Thereafter, the catheter releases the stent towards the lesion. Then, the stent forcibly pushes the lesion portion, which has blocked a portion of an inner cavity, outwards so that space can be secured in the inner cavity, thus enabling the flow of not only blood but also endocrine secretions such as bile.

A representative example of conventional catheters for stent surgery was proposed in Korean Patent Laid-open Publication No. 10-2010-0086294.

The conventional catheter for stent surgery functions to move a stent along a guide wire towards a lesion portion on which stenosis has occurred or is in progress. The catheter includes an outer tube part, a movable tube part and a stent part. The outer tube part includes an outer tube which is connected to a handle body and has an outlet hole through which the guide wire comes out of the outer tube. The movable tube part includes a movable tube which is connected to a front end of a push rod which is inserted into the outer tube through the handle body of the outer tube part. The movable tube has therein an outlet hole through which the guide wire comes out of the movable tube. The stent part includes an installation tube in which a stent disposed on the front end of the movable tube of the movable tube part is installed while being reduced in volume. A rear end of the installation tube is partially inserted into a front end of the outer tube.

This conventional catheter further includes a cylindrical-tube-shaped reinforcing member which is coupled to the outer tube and encloses the outer circumferential surface of the outer tube in such a way that the outlet hole of the outer tube is exposed to the outside so as to prevent a part of the outer tube that defines the outlet hole from being bent during surgery. The reinforcing member has a wire hole through which the guide wire comes out of the reinforcing member.

The conventional catheter having the above-mentioned construction is configured to reduce the length of the guide wire. As the length of the guide wire is reduced, handling in setting a guide direction is facilitated, and the production cost can be reduced.

However, the conventional catheter for stent surgery has a problem in which when the guide wire which moves forwards or backwards through the outlet hole of the outer tube is inserted into the outer tube, it may make contact with the inner tube and become entangled with the inner tube, whereby the guide wire may not be smoothly moved forwards or backwards.

As such, in the conventional catheter, because the guide wire may make contact with the inner tube or become entangled with it, the guide wire cannot be reliably moved to the target location that an operator wants, thus making the stent surgery difficult.

DISCLOSURE

Technical Problem

Accordingly, the present invention has been made keeping in mind the above problems occurring in the prior art, and an object of the present invention is to provide a monorail which can guide a guide wire in a precise direction when the guide wire enters an outer tube and comes out of it.

Another object of the present invention is to provide a monorail in which a separation guide is fixed in the outer tube so that the direction in which the guide wire and the inner tube are guided is maintained constant without change, whereby forward and backward movement of the guide wire can be reliably performed.

A further object of the present invention is to provide a monorail in which a separation guide which is separately manufactured can be used in the existing catheter, thus enhancing compatibility.

Technical Solution

In order to accomplish the above objects, the present invention provides a monorail of a catheter for stent surgery, the catheter including an outer tube having an outer hole, an inner tube installed in the outer tube, and a guide wire introduced into the outer hole and the inner tube and protruded outwards from a front end of the inner tube so that the outer tube and the inner tube move along the guide wire so as to be guide a stent to a target surgical location for installation of the stent, wherein the monorail is provided in the catheter so as to space the guide wire apart from the inner tube and guide the guide wire and comprises a separation guide inserted into and fixed in the outer tube and configured such that the guide wire that is introduced into the outer hole is spaced apart from the inner tube without making contact with the inner tube.

Advantageous Effects

According to the present invention, a guide wire can be guided in a precise direction when the guide wire enters an outer tube and comes out of it.

Furthermore, a separation guide is fixed in the outer tube so that the direction in which the guide wire and the inner tube are guided is maintained constant without change, whereby forward and backward movement of the guide wire can be reliably performed.

In addition, a separation guide which is separately manufactured can be used in the existing catheter, thus enhancing the compatibility.

DESCRIPTION OF THE REFERENCE NUMERALS IN THE DRAWINGS

Figure 1:
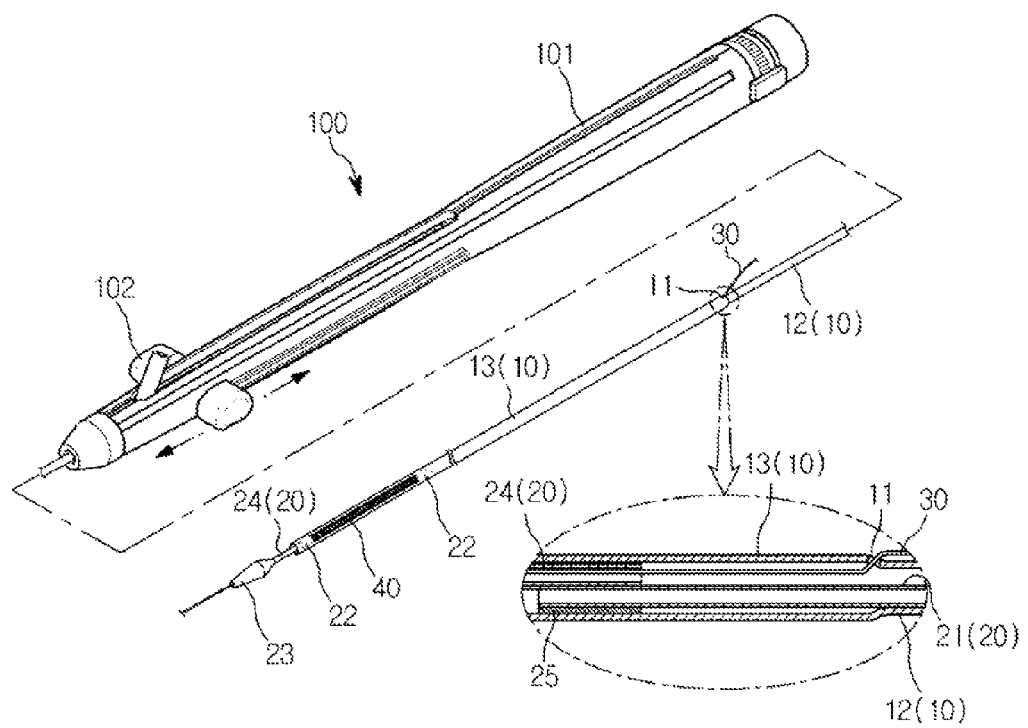
FIG. 1 is a perspective view showing a typical catheter for stent surgery.

10: outer tube 11: outer hole
12: small diameter part 13: large diameter part
20: inner tube 21: first tube
22: fixed tip 23: tip
24: second tube 25: connection tube
30: guide wire 40: stent
50: separation guide 51: wire receiving depression
52: tube receiving depression 53: perpendicular end
54: guide end 100: catheter
101: handle 102: operating member

BEST MODE

The present invention provides a monorail which can reliably guide a guide wire introduced into an outer tube such that an entry direction and an exit direction of the guide wire are prevented from changing.

Mode for Invention

Hereinafter, a preferred embodiment of the present invention will be explained in detail with reference to the attached drawings.

As shown in FIG. 1, a monorail according to the present invention is a device for spacing a guide wire 30 apart from an inner tube 20 and guiding the guide wire 30 in a catheter 100 for stent surgery. In the catheter 100, a guide wire 30 is inserted, through an outer hole 11 of the outer tube 10, into the inner tube 20 installed in the outer tube 10 and then protruded outwards from a front end of the inner tube 20. The inner tube 20 and the outer tube 10 move along the guide wire 30, thus guiding a stent 40 to a target surgical location for installation of the stent 40.

First, the catheter 100 will be described in brief. The catheter 100 includes a handle 101 which is grasped by the hand of a user, and an operating member 102 which moves along a fixed rod (not shown) which is longitudinally installed in the handle 101.

The outer tube 10 is connected to a front end of the operating member 102.

When the operating member 102 is moved forwards or backwards, the outer tube 10 is also moved forwards or backwards.

The inner tube 20 which is inserted into the outer tube 10 is connected and fixed to a front end of the fixed rod.

The inner tube 20 includes a first tube 21 which is connected and fixed to the fixed rod.

In addition, a pair of fixed tips 22 are provided in the inner tube 20 so as to define an area in which the stent 40 is installed. A second tube 24 which is integrally includes a conical tip 23 is provided on the front end of the inner tube 20 in which the fixed tips 22 are installed.

Although the fixed tip 22 may be made of plastic or metal, in this embodiment of the present invention, it is illustrated as being made of tungsten.

A rear end of the second tube 24 partially overlaps a front end of the first tube 21, and a cylindrical connect tube 25 is used to connect the rear end of the second tube 24 to the front end of the first tube 21.

The outer hole 11 is formed in a medial portion or a front portion of the entire length of the outer tube 10.

The outer tube 10 includes a small diameter part 12 which is connected to the operating member 102, and a large diameter part 13 which is larger in diameter than the small diameter part 12 and integrally extends forwards from the small diameter part 12. The outer hole 11 is formed in the large diameter part 13 at a position adjacent to the junction between the small diameter part 12 and the large diameter part 13.

The portions of the first and second tubes 21 and 24 that are connected to each other by the connection tube 25 are disposed in the large diameter part 13 of the outer tube 10.

Figure 2:
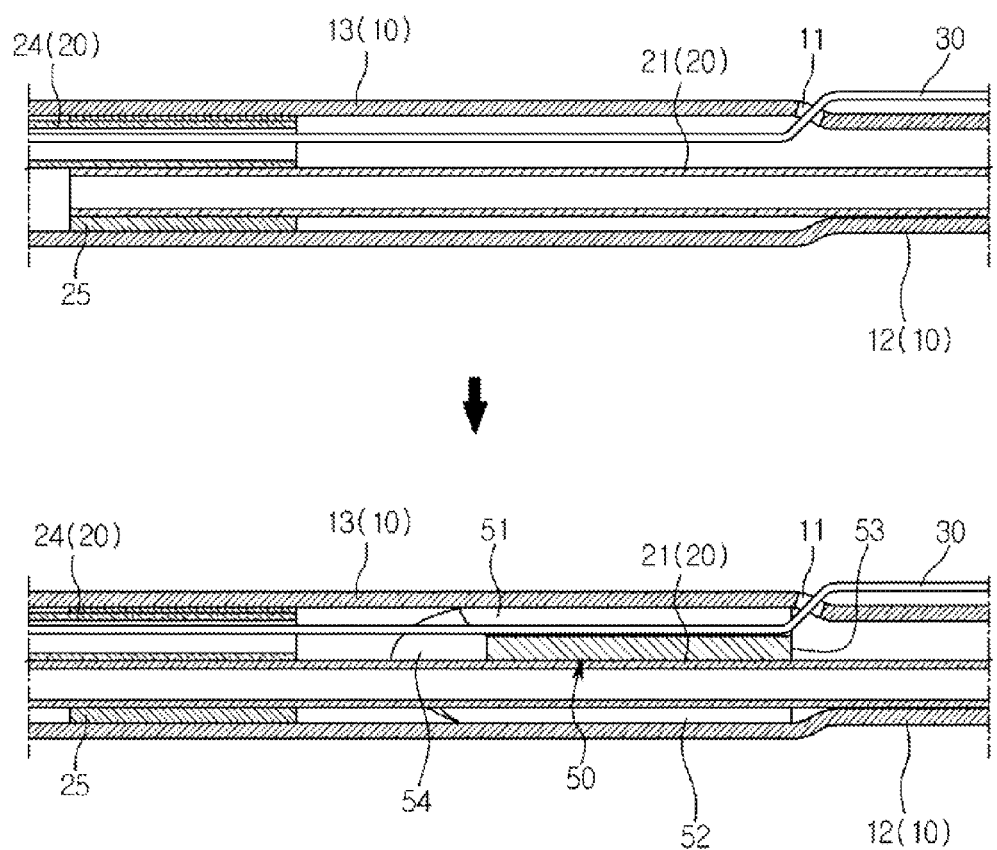
FIG. 2 is of partial sectional views showing the case where a monorail according to the present invention is not used in a catheter for stent surgery and the case where the monorail is used therein.

As shown in FIG. 2, a separation guide 50 is inserted into and fixed in the outer tube 10.

As such, if the separation guide 50 is inserted into the outer tube 10, the guide wire 30 which is inserted into the outer hole 11 is spaced apart from the inner tube 20 by the separation guide 50 such that the guide wire 30 can be inserted into or protruded from the outer tube 10 without making contact with the inner tube 20.

Figure 3A:
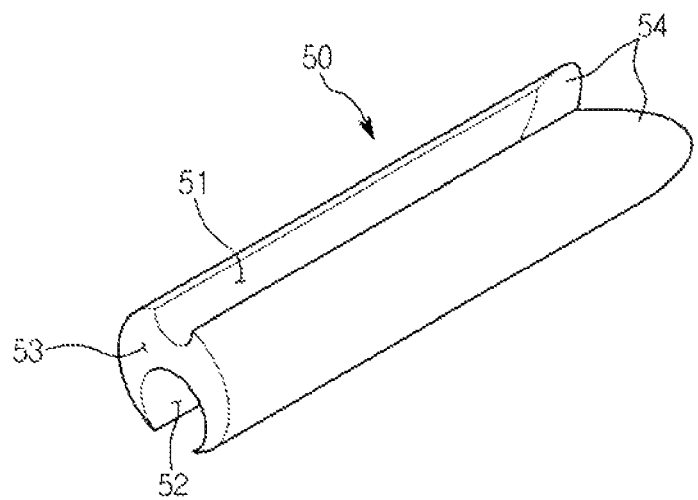
FIG. 3a is a perspective view of the monorail.
Figure 3B:
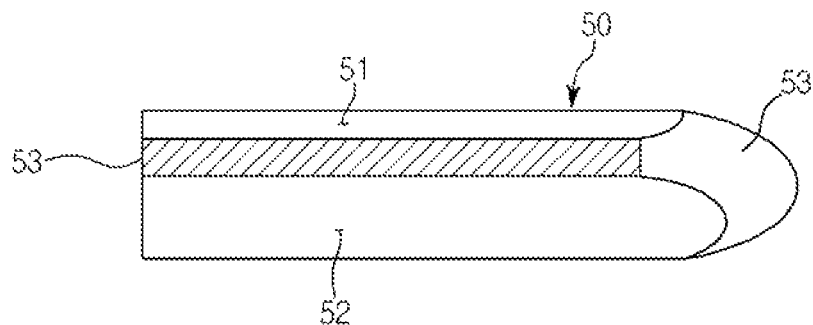
FIG. 3b is a longitudinal sectional view of the monorail.
Figure 3C:
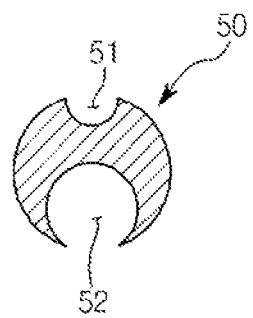
FIG. 3c is a cross-sectional view of the monorail.
Figure 4:
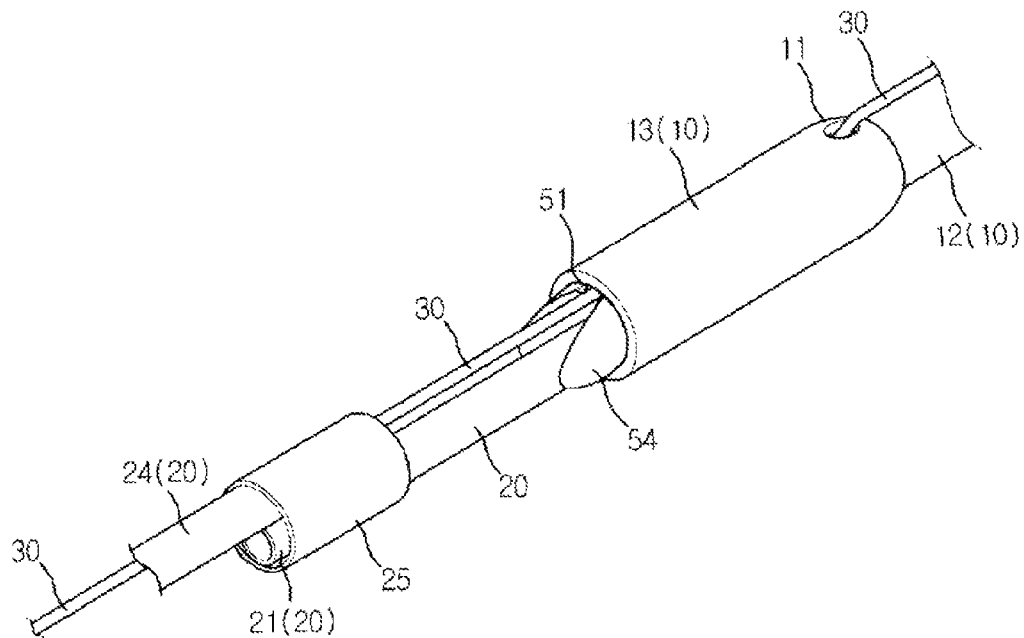
FIG. 4 is a partial perspective view illustrating the monorail according to the present invention used in the catheter for stent surgery.

As shown in FIGS. 3a to 4, the separation guide 50 has a cylindrical shape. A wire receiving depression 51 is longitudinally formed in a first side of an outer circumferential surface of the separation guide 50 so that the guide wire 30 is inserted into and guided along the wire receiving depression 51.

A tube receiving depression 52 is longitudinally formed in a second side of the outer circumferential surface of the separation guide 50 so that the inner tube 20 is inserted into the tube receiving depression 52.

The wire receiving depression 51 and the tube receiving depression 52 of the separation guide 50 are formed to be spaced apart from each other.

In detail, the wire receiving depression 51 and the tube receiving depression 52 have circular arc-shaped cross sections and are longitudinally formed in the outer circumferential surface of the separation guide 50 at diametrically opposite positions. The diameter of wire receiving depression 51 is larger than that of the guide wire 30. The diameter of the tube receiving depression 52 is larger than that of the first tube 21 of the inner tube 20.

A first end of the separation guide 50 forms a perpendicular end 53 which has a surface perpendicular to an axis of the separation guide 50. A second end of the separation guide 50 forms semicircular guide ends 54 which face each other and are formed by cutting a central portion of the second end in a V shape such that portions of the wire receiving depression 51 and the tube receiving depression 52 are cut out.

The perpendicular end 53 faces the small diameter part 12. The guide ends 54 face the front of the outer tube 10. The guide wire 30 and the inner tube 20 that are respectively inserted into the wire receiving depression 51 and the tube receiving depression 52 are guided by the guide ends 54, whereby the guide wire 30 and the inner tube 20 can be disposed at positions spaced apart from each other.

Further, the separation guide 50 is disposed behind the connection tube 25 which connects the first tube 21 to the second tube 24. The separation guide 50 is fixed in the large diameter part 13 of the outer tube 10. The second tube 24 is fitted into the tube receiving depression 52 such that the second tube 24 cannot be move forwards or backwards relative to the tube receiving depression 52. The guide wire 30 is disposed in the wire receiving depression 51 so as to be movable forwards and backwards.

The diameter of the separation guide 50 is the same as the inner diameter of the outer tube 10 so that the separation guide 50 is tightly fitted into the outer tube 10. Furthermore, after the separation guide 50 is fitted into the outer tube 10, a bonding agent may be used to more reliably fix them to each other.

The operation and effect of the present invention having the above-mentioned construction will be explained.

As shown in FIGS. 2 to 4, in the catheter 100, the separation guide 50 is inserted into the front end of the outer tube 10.

Here, the separation guide 50 is oriented such that the wire receiving depression 51 is disposed just below the outer hole 11, and the tube receiving depression 52 faces a lower portion of the inner surface of the outer tube 10.

In detail, the separation guide 50 is disposed such that the perpendicular end 53 of the separation guide 50 faces the rear end of the first tube 21, and the guide ends 54 face the connection tube 25 and the second tube 24

The separation guide 50 is oriented in such a way that the wire receiving depression 51 of the separation guide 50 is on the same straight line as the second tube 24.

The separation guide 50 may be fixed in the outer tube 10 by force-fitting. Preferably, the separation guide 50 is fixed to the outer tube 10 by bonding to reliably prevent the separation guide 50 from rotating relative to the outer tube 10.

Thereafter, the guide wire 30 is inserted into the outer tube 10 through the outer hole 11 rather than through the handle 101 of the catheter 100 and is inserted into the wire receiving depression 51 of the separation guide 50.

An end of the guide wire 30 that is inserted into the outer tube 10 enters the second tube 24 of the inner tube 20, passes through the second tube 24, and is exposed out of the front end of the second tube 24 through the tip 23.

Figure 5:
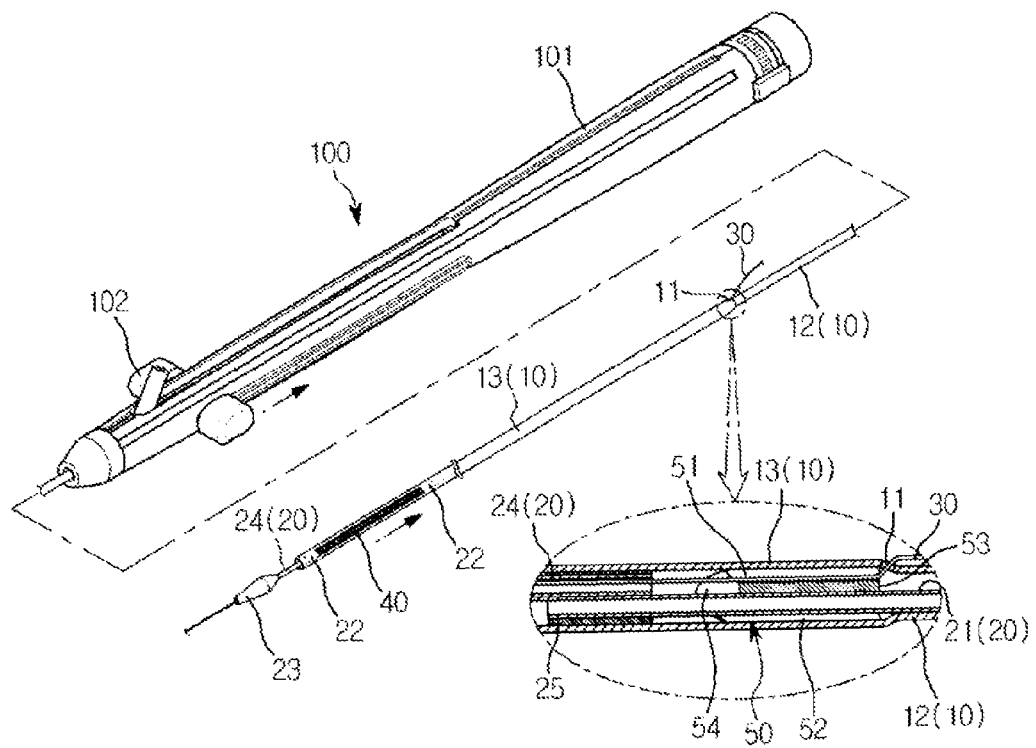
FIG. 5 is a perspective view illustrating the monorail according to the present invention used in the catheter for stent surgery.
Figure 6:
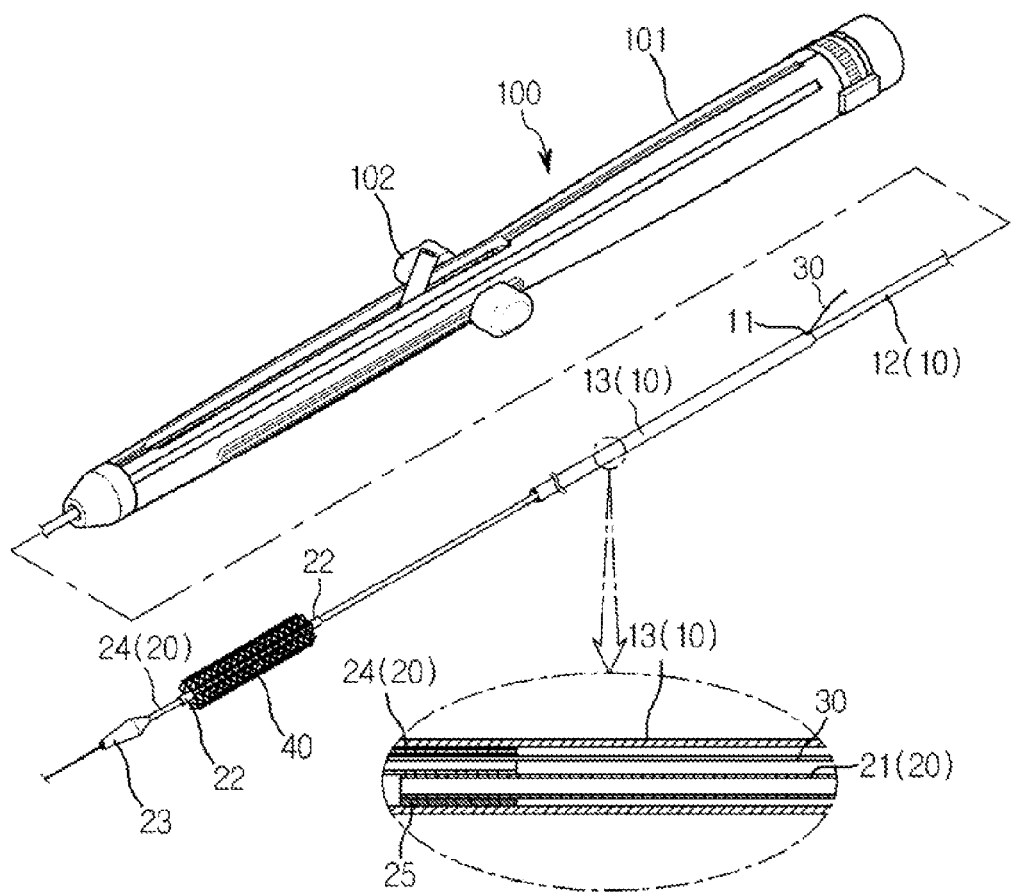
FIG. 6 is a perspective view showing the exposure and expansion of a stent of the catheter provided with the monorail according to the present invention.

As shown in FIGS. 5 and 6, the guide wire 30 that is exposed to the outside is inserted into a cavity, particularly, in this embodiment, the carotid artery, of the body of a patient in which a lesion requiring installation of the stent 40 is formed. When the stent 40 is located at the cavity of the body of the patient in which the lesion is formed, the operating member 102 is moved backwards so that the outer tube 10 is moved backwards and, simultaneously, the stent 40 that has been pressed and installed between the fixed tips 22 of the inner tube 20 is expanded and exposed out of the inner tube 20.

That is, when the guide wire 30 is inserted into the outer tube 10 through the outer hole 11 in order to install the stent 40, the guide wire 30 enters the wire receiving depression 51 of the separation guide 50 and thus does not make contact with the inner tube 20, thereby preventing a problem of the guide wire 30 being entangled with the inner tube 20.

Furthermore, when the guide wire 30 is operated forwards or backwards to move towards the lesion, it moves along the wire receiving depression 51 of the separation guide 50. Therefore, the guide wire 30 can reliably and correctly move forwards or backwards.

In addition, the inner tube 20 is inserted into and fixed to the tube receiving depression 52 of the separation guide 50. Thus, when the operating member 102 of the catheter 100 is moved forwards or backwards, the first tube 21 which is fitted in the tube receiving depression 52 of the separation guide 50 is moved along with the separation guide 50 by movement of the outer tube 10. As such, the outer and inner tubes 10 and 20 do not change in position relative to each other, thus preventing a problem of the outer and inner tubes 10 and 20 being twisted.

To conclude, by virtue of the separation guide 50 used in the catheter 100, the guide wire 30 can be maintained in a state of being separated from the inner tube 20 without being entangled with the inner tube 20. Furthermore, the forward or backward movement of the guide wire 30 can be reliably conducted without being twisted, thus making it possible to reliably guide the stent 40 to a precise position.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

The invention claimed is:

1. A monorail of a catheter for stent surgery, the catheter comprising an outer tube having an outer hole, an inner tube installed in the outer tube, and a guide wire introduced into the outer hole and the inner tube and protruded outwards from a front end of the inner tube so that the outer tube and the inner tube move along the guide wire so as to be guide a stent to a target surgical location for installation of the stent, wherein the monorail is provided in the catheter so as to space the guide wire apart from the inner tube and guide the guide wire and comprises a separation guide inserted into and fixed in the outer tube and configured such that the guide wire that is introduced into the outer hole is spaced apart from the inner tube without making contact with the inner tube, wherein the outer tube comprises a small diameter part connected to the operating member, and a large diameter part integrally extending forwards from the small diameter part, the large diameter part being larger in diameter than the small diameter part, the outer hole is formed in the large diameter part at a position adjacent to a junction between the small diameter part and the large diameter part, and a first end of the separation guide forms a perpendicular end having a surface perpendicular to an axis of the separation guide, and a second end of the separation guide forms semicircular guide ends facing each other, the semicircular guide ends being formed by cutting a central portion of the second end in a V shape such that portions of the wire receiving depression and the tube receiving depression are cut out, wherein the perpendicular end faces the small diameter part, the guide ends face a front of the outer tube, and the guide wire and the inner tube that are respectively inserted into the wire receiving depression and the tube receiving depression are guided by the guide ends.

2. The monorail of claim 1, wherein the separation guide inserted into the outer tube has a cylindrical shape, with a wire receiving depression longitudinally formed in a first side of an outer circumferential surface of the separation guide so that the guide wire is introduced into and guided along the wire receiving depression, and a tube receiving depression longitudinally formed in a second side of the outer circumferential surface of the separation guide so that the inner tube is inserted into the tube receiving depression.

3. The monorail of claim 2, wherein the wire receiving depression and the tube receiving depression are spaced apart from each other.

* * * * *